United States Patent [19]

Englert et al.

[11] Patent Number: 4,661,636

[45] Date of Patent: Apr. 28, 1987

[54] 6-SULFOXYPHENOL DERIVATIVES, THEIR PREPARATION AND THEIR USE AS CYTOPROTECTIVE AGENTS

[75] Inventors: Heinrich C. Englert; Hans-Jochen Lang, both of Hofheim am Taunus; Dieter Mania, Kelkheim; Martin Bickel, Frankfurt am Main, all of Fed. Rep. of Germany

[73] Assignee: Hoechst Aktiengesellschaft, Fed. Rep. of Germany

[21] Appl. No.: 648,139

[22] Filed: Sep. 7, 1984

[30] Foreign Application Priority Data

Sep. 10, 1983 [DE] Fed. Rep. of Germany ....... 3332780

[51] Int. Cl.$^4$ .................. C07C 149/00; C07C 149/32
[52] U.S. Cl. ...................................... 568/31; 568/27; 568/442; 548/301; 549/39
[58] Field of Search ................. 568/31, 23, 28, 27, 568/342, 442, 437; 548/301; 549/39

[56] References Cited

U.S. PATENT DOCUMENTS

| | | | |
|---|---|---|---|
| 3,780,110 | 12/1973 | Gay | 568/437 |
| 3,804,883 | 4/1974 | Galantay | 568/437 |
| 3,917,704 | 11/1975 | Kaiser et al. | 568/31 |

FOREIGN PATENT DOCUMENTS

| | | | |
|---|---|---|---|
| 0044807 | 1/1982 | European Pat. Off. | 548/301 |
| 0070779 | 7/1982 | European Pat. Off. | 548/301 |
| 2,512,614 | 2/1975 | Fed. Rep. of Germany | 568/437 |
| 2370041 | 6/1978 | France | 548/301 |
| 1233969 | 6/1971 | United Kingdom | 568/31 |

OTHER PUBLICATIONS

Chemical Abstracts Service, Registry Handbook, 1965–1971, p. 3204 R.

Journal of the Chemical Society (1978), pp. 633–638.

*Primary Examiner*—Werren B. Lone
*Attorney, Agent, or Firm*—Finnegan, Henderson, Farabow, Garrett & Dunner

[57] ABSTRACT

Compounds of the formula I

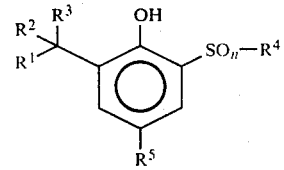

where $R^1$ is hydrogen, lower alkyl, lower alkoxy, amino or dialkylamino; $R^2$ and $R^3$ are O-alkyl, N-dialkyl or S-alkyl, or $R^2$ and $R^3$ together represent —X—(CH$_2$)$_m$—X, a carbonyl group or an imino group NR, and m is 2–6; where $R^4$ is lower alkyl, cycloalkyl, alkenyl or dialkylamino, and where $R^5$ is lower alkyl or cycloalkyl, and where n is 1 or 2, have excellent cytoprotective effects.

They are prepared by reacting compounds II

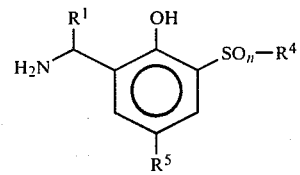

with formaldehyde or a reagent producing formaldehyde.

15 Claims, No Drawings

6-SULFOXYPHENOL DERIVATIVES, THEIR PREPARATION AND THEIR USE AS CYTOPROTECTIVE AGENTS

The invention relates to 6-sulfoxyphenol derivatives of the general formula I

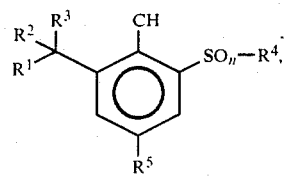

in which $R^1$ represents hydrogen, alkyl having 1 to 4 carbon atoms, $OR^7$, $R^7$ denoting hydrogen or alkyl having 1 to 4 atoms, or $NR^8R^9$, $R^8$ and $R^9$ being identical or different and denoting hydrogen or alkyl having 1 to 4 carbon atoms; $R^2$ and $R^3$ are identical or different and represent $OR^{10}$, $NR^{10}R^{11}$ or $SR^{10}$, $R^{10}$ and $R^{11}$ being identical or different and representing alkyl having 1 to 8 carbon atoms, or $R^2$ and $R^3$ together form a $-X-(CH_2)_m-X-$chain, X representing O, S or $NR^{11}$ and m denoting 2 to 6, or $R^2$ and $R^3$ together represent a carbonyl group $=O$ or an imino group $=N-R^{11}$; $R^4$ represents alkyl having 1 to 4 carbon atoms, cycloalkyl having 3 to 6 carbon atoms or alkenyl having 2 to 4 carbon atoms and up to 2 double bonds, each having up to 3 halogen atoms, or represents $NR^{12}R^{13}$, $R^{12}$ and $R^{13}$ being identical or different and denoting hydrogen or alkyl having 1 to 4 carbon atoms; $R^5$ resents alkyl having 1 to 10 carbon atoms or cycloalkyl having 3 to 8 carbon atoms and up to 8 ring members, or represents halogen; and n is 1 or 2.

Preferred compounds of the formula I are those in which $R^1$ represents hydrogen or OH; $R^2$ and $R^3$ together form a carbonyl group or a

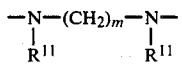

chain, m being 2 or 3 and $R^{11}$ denoting methyl or ethyl; $R^4$ denotes methyl or $NH_2$; $R^5$ denotes alkyl having 4 to 8 carbon atoms, and n denotes 1 or 2.

Particularly preferred compounds of the formula I are those where $R^1$ represents hydrogen, $R^2$ and $R^3$ together represent a carbonyl group, $R^4$ represents methyl, $R^5$ represents alkyl having 4 to 8 carbon atoms, and n represents 1 or 2. Those compounds in which $R^5$ denotes 1,1-dimethylethyl and n denotes 2 have proved to be particularly useful; as have those compounds where $R^5$ is 1,1-dimethylethyl and n is 1.

Another preferred compound of the general formula I is one where $R^1$ represents hydrogen, $R^2$ and $R^3$ together represent a carbonyl group, $R^4$ represents chloromethyl, $R^5$ represents 1,1-dimethylethyl and n represents 2; also a compound where $R^1$ represents hydrogen, $R^2$ and $R^3$ together represent a carbonyl group, $R^4$ represents $NH_2$, $R^5$ represents 1,1-dimethylethyl and n is 2. Likewise of particular importance is a compound where $R^1$ represents hydrogen, $R^2$ and $R^3$ together represent

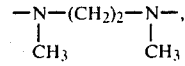

$R^4$ represents methyl, $R^5$ represents 1,1-dimethyl-ethyl and n is 2.

Especially preferred compounds according to formula I are those in which $R^1$ represents hydrogen or OH; $R^2$ and $R^3$ together represent a carbonyl group $=O$; $R^4$ denotes $NR^{12}R^{13}$, $R^{12}$ and $R^{13}$ being identical or different and denoting hydrogen or alkyl having 1 to 4 carbon atoms; $R^5$ represents alkyl having 3 to 8 carbon atoms; and n represents 2.

The invention also relates to a process for the preparation of a compound of the general formula I, which comprises (a) reacting compounds of the formula II

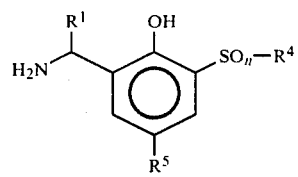

in which $R^1$ denotes hydrogen or alkyl having 1 to 4 carbon atoms, $R^4$, $R^5$ and n have the abovementioned meanings, but $R^4$ can also represent a group $-N=Z$, Z having the meaning of a protective group of the formula V

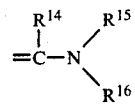

in which the radicals $R^{14}$ denote hydrogen or alkyl having 1 to 4 carbon atoms, and $R^{15}$ and $R^{16}$ denote alkyl having 1 to 4 carbon atoms, with formaldehyde, or a reagent producing formaldehyde, to give compounds of the formula I and, where appropriate, eliminating the protective group Z by hydrolysis;

(b) reacting compounds of the formula III

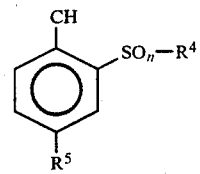

in which $R^4$, $R^5$ and n have the abovementioned meanings, but $R^4$ can also have the meaning $-N=Z$ defined under process variant (a), with a formylating reagent to give compounds of the general formula I and, where appropriate, eliminating the protective group Z by hydrolysis;

(c) oxidizing compounds of the general formula IV

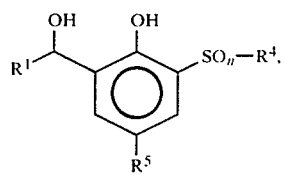

in which $R^1$, $R^4$, $R^5$ and n have the abovementioned meanings, but $R^4$ can also have the meaning —N=Z defined under process variant (a), to give compounds of the general formula I and, where appropriate, eliminating the protective group Z by hydrolysis;

(d) oxidizing compounds of the formula I, in which $R^1$ represents hydrogen, $R^2$ and $R^3$ together represent a carbonyl group, and $R^4$ and $R^5$ have the abovementioned meanings, but $R^4$ can also have the meaning —N=Z described under process variant (a), to give compounds of the general formula I and, where appropriate, eliminating the protective group Z by hydrolysis and, where appropriate, converting the resulting acids into their esters or amides of the general formula I;

(e) converting compounds of the general formula I, in which $R^1$ represents hydrogen or alkyl having 1 to 4 carbon atoms; $R^2$ and $R^3$ together form a carbonyl group; and $R^4$, $R^5$ and n have the abovementioned meanings, using alcohols $R^{10}OH$, thioalcohols $R^{10}SH$, amines $NHR^{10}R^{11}$ and using compounds $HX—(CH_2)_m—XH$, $R^{10}$, $R^{11}$, X and m having the abovementioned meanings, into the corresponding acetals, thioacetals, aminals or imines of the general formula I;

(f) chlorosulfonating compounds of the general formula XVII

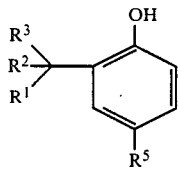

and either reacting the resultant sulfonyl chlorides

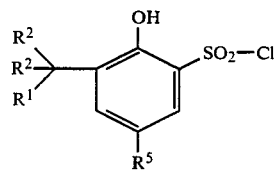

with amines

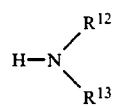

to give compounds I, or subjecting them to reduction to give the sulfinic acids XIX

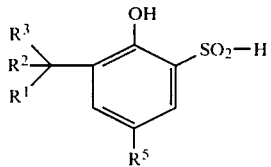

and converting the latter by alkylation into the compounds

In addition, the invention relates to the use of a compound of the general formula I for the treatment and prophylaxis of damage to the mucosa, the gastrointestinal tract and of damage to the liver, pancreas and vascular system In addition, the inVention relates to the use of a compound of the general formula VII

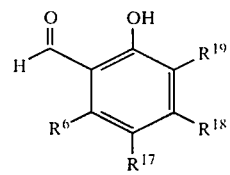

in which $R^6$, $R^{17}$, $R^{18}$ and $R^{19}$ represent hydrogen or halogen, in particular this type of compound of the formula VII where $R^6$ and $R^{18}$ are hydrogen, and $R^{17}$ and $R^{19}$ are hydrogen or halogen, as cytoprotective agents.

Moreover, the invention relates to the use of salicylaldehyde, of 2-formyl-4,6-dichlorophenol, and of 2-formyl-4,6-dibromophenol, as compounds of the formula VII, as cytoprotective agents.

Compounds of the general formula I are new. When administered to rats, they show pronounced cytoprotective properties which were unexpected for compounds of this type.

When compounds of the formula I have chiral carbon and/or sulfur atoms, then the invention relates to compounds of both the R and the S configurations. It is then possible for the compounds to exist in all conceivable diastereomeric forms, as racemates, pure enantiomers or as mixtures of these.

In general, it is necessary to use an acid catalyst for the reaction of benzylamines II to give compounds of the general formula I by process variant (a). The benzylamines can be used as such or in the form of their acid addition salts, and it is also possible to use, in place of formaldehyde, precursors which very readily liberate formaldehyde, such as, for example, paraformaldehyde or urotropine (hexamethylenetetraamine). Acid catalysts are all commonly used mineral acids, but organic acids, such as, for example, alkanoic acids, are also advantageous since these can also serve directly as the solvent. It has emerged that it is particularly advantageous to use the HCl addition salts of the benzylamines II, it being possible to react them smoothly with urotropine in trifluoroacetic acid to give the compounds I. The reaction temperature can vary within wide limits, temperatures between 40° and 120° C. being advantageous. In general, the process is advantageously carried out at the reflux temperature of the solvent used. Particularly when using urotropine, it can be advantageous to add small amounts of strong aqueous mineral acids, such as, for example, 4N hydrochloric acid, towards the end of the reaction in order to improve the yield. However, when commercially available trifluoroacetic acid is used as the solvent, this is usually unnecessary. On the other hand, this is indispensable when compounds I where $R^4$ is $NH_2$ are prepared, since this entails elimination of the above-mentioned group Z.

The reaction mixtures are worked up either by distilling out the solvent or by diluting with a non-solvent, such as, for example, water. This usually results in products in the crystalline form, and these can be further purified by recrystallization from suitable commonly used solvents or by chromatography. Additional purification is unnecessary in many cases.

The benzylamines II can be readily prepared by processes known from the literature, for example by amidoalkylation of phenols III using N-hydroxymethylcarboxamides of the general formula VI, with acid catalysis:

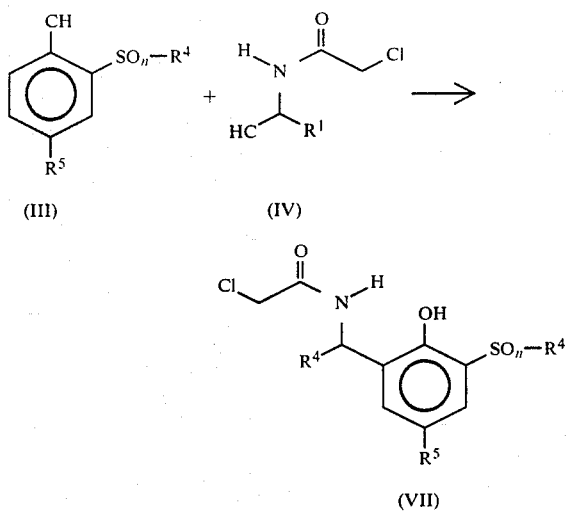

(III)        (IV)

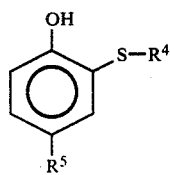

(VII)

The amides VIII produced in this reaction can be readily converted into the benzylamines II by acid hydrolysis. In this context, the radicals $R^4$, $R^5$ and n have the abovementioned meanings, and $R^1$ is H or $C_1$-$C_4$-alkyl.

It is possible to prepare the phenols of the general formula III by a variety of processes. One method, for example, comprises oxidizing thioethers of the general formula IX

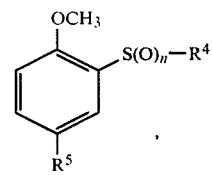  IX in which the radicals $R^4$ and $R^5$, and n, have the abovementioned meanings. Oxidations of this type are known from the literature. It is also known that, by selecting the reaction conditions, either sulfoxides (n=1) or sulfones (n=2) can be obtained.

The thioethers of the general formula IX can be prepared from the phenols of the formula X, in which $R^5$ has the abovementioned meaning, in a manner known per se; for example by the action of a sulfoxide $R^4$—SO—$R^4$ in the presence of perchloric acid and phosphorus oxychloride, or by reaction with a sulfenyl chloride $R^4$—S—Cl in a manner known per se, in each instance $R^4$ having the abovementioned meaning.

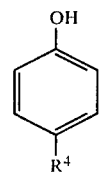   X

Phenols X can readily be prepared by standard methods (cf. Houben-Weyl, Methoden der org. Chem. -Phenole (Methods of Org. Chem. - Phenols) Part 2, pages 925 et seq., published by G. Thieme, Stuttgart, 1976).

Another method for the preparation of phenols of the general formula III, in which $R^5$ and $R^4$ have the abovementioned meanings and n is 2, comprises ether cleavage of anisoles of the general formula XI, with the corresponding meanings of $R^5$, $R^4$ and n.

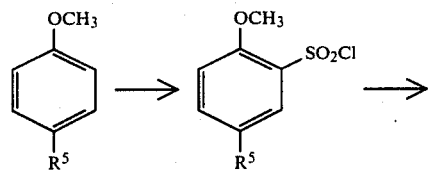 XI

This is carried out in a manner known per se by the action of mineral acids, such as hydriodic acid, or of Lewis acids, such as aluminum chloride or boron tribromide, in inert solvents, such as, for example, methylene chloride or chloroform. It is also possible to carry out successfully the commonly used cleavage by pyridinium hydrochloride at temperatures above 180° C.

Compounds of the general formula XI where n is 2 are prepared from the anisols XII by a sequence of standard methods known per se:

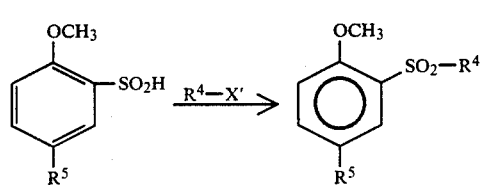

XII        XIII

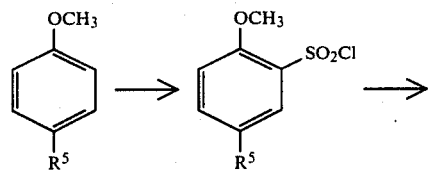

XIV        XI

Sulfonyl chlorides XIII are obtained in a manner known per se by the action of chlorosulfuric acid on anisoles XII. This reaction is advantageously carried out in an inert solvent, such as chloroform or methylene chloride. When $R^5$ in XII represents higher alkyl, a temperature range of 0°-20° C. should be maintained, and the excess of chlorosulfonic acid, which is customary per se, should not be greater than 3 equivalents.

The reduction to give the sulfinic acids XIV can be carried out by a wide variety of processes (cf. Houben-Weyl, Methoden der org. Chemie., Volume X, pages 563 et seq., published by G. Thieme, Stuttgart, 1955). Reduction with sodium sulfite in the presence of sodium hydroxide in solutions in aqueous acetone has proved to be a simple and efficient method.

The alkylation of sulfinic acids to give sulfones is a reaction known per se, it preferably being carried out under base catalysis. In the case of the sulfinic acids XIV, alkyl iodides have proved to be particularly suitable alkylating agents $R^4$—$X'$, $R^4$ having the abovementioned meaning and $X'$ representing halogen, preferably iodine. The bases which are advantageously employed are organic bases, such as triethylamine in solution in acetone, as well as inorganic bases, such as LiOH, NaOH, KOH etc. in solution in water or aqueous acetone.

If $R^4$ represents an α-halogenoalkyl radical, a number of variants of this alkylation reaction can be used advantageously, such as, for example, reaction of sulfinic acids with α-dihalogenocarboxylic acids in the presence of $K_2CO_3$, the β-sulfonyl-α-halogenocarboxylic acid which is formed as an intermediate eliminating $CO_2$ in a manner known per se with the formation of the α-halogenomethylsulfonyl radical.

The anisoles XII are prepared from the phenols X by standard methods (Organikum, VEB Deutscher Verlag der Wissenschaften, Berlin 1971, page 222).

Phenols of the general formula III, in which $R^4$ has the meaning $NR^{12}R^{13}$ or —N=Z, $R^{12}$ and $R^{13}$ having the abovementioned meanings, can be readily prepared by standard methods. The sulfonamides XV are obtained by the action of amines $NHR^{12}R^{13}$ on the sulfonyl chlorides XIII.

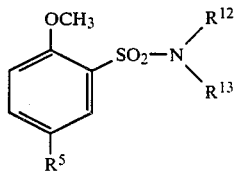

XV

In the case where $R^{12}$ and $R^{13}$ have the meaning of hydrogen, it is possible to convert the sulfonamides XV into the protected sulfonamides XVI, where appropriate in analogy to the description in German Offenlegungsschrift No. 2,658,766 or that in German Offenlegungsschrift No. 2,461,601, by introducing substituted formamides, for example dimethylformamide, in the presence of a reagent favoring the elimination of water, such as thionyl chloride or phosphorus oxychloride. In place of the formamides, it is also possible to use their acetals, such as, for example, dimethylformamide dimethyl acetal, and in this case the reaction then usually takes place without any addition of condensing agent.

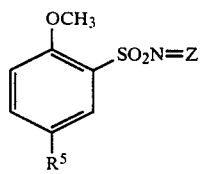

XVI

It is also possible to convert the anisoles XV and XVI into the corresponding phenols III by ether cleavage as described for the anisoles XI.

If compounds I, especially those in which $R^2$ and $R^3$ together represent a carbonyl group and $R^1$ denotes hydrogen, are prepared from the phenols III by process variant (b), then this is carried out in a manner known per se by all formylation reactions which are suitable for phenols, for example those described in "Advanced Organic Chemistry", Jerry March, Mc-Graw-Hill, Series in Advanced Chemistry, McGraw-Hill Kogakusha Ltd., 1977, page 1167.

The use of the Duff reaction (see Chem. Rev. 38, 230 et seq. (1946)) has proved to be particularly advantageous, for example using urotropine in an acid organic solvent, such as, for example, alkanoic acids. In this instance, it is very particularly advantageous to use trifluoroacetic acid. Conditions for carrying out and working up the reaction which are identical to those described under process variant (a) can be used and are advantageous.

If compounds I are prepared from compounds IV by oxidation by process variant (c), in principle this can be carried out with all commonly used oxidizing agents. Examples which may be mentioned are $KMnO_4$, bromine, $MnO_2$, $RhO_4$, $CrO_3$, $Na_2Cr_2O_7$, silver salts, such as $Ag_2CO_3$ and $Ag_2O$, pyridinium chlorochromate and many more as are described in, for example, "Advanced Organic Chemistry", Jerry March, McGraw-Hill Kogakusha Ltd., 1977, pages 1082–1088, for reactions of this type. For example, the use of $Na_2Cr_2O_7$ with the addition of mineral acids, such as sulfuric acid, in a two-phase system of water and an organic solvent, such as, for example, diethyl ether, has proved to be particularly advantageous. If $R_1$ in compounds IV represents hydrogen, the use of pyridinium chlorochromate in chlorinated hydrocarbons, for example methylene chloride, is also of importance, particularly when the intention is to prepare compounds I where $R^1$ is H.

Compounds IV can be prepared by a variety of routes. One possibility, for example, comprises subjecting the phenols III to hydroxymethylation. In general, this process entails reacting their alkali metal salts, for example the sodium salts, in aqueous solution with formaldehyde or a reagent generating formaldehyde, such as, for example, paraformaldehyde. Compounds IV where $R^1$ is H are then obtained in a manner known per se.

Compounds IV with $R^1$ having the meaning of lower alkyl can also be obtained in a manner known per se by reaction of compounds of the general formula I, where $R^1$ is H and $R^2$ and $R^3$ are carbonyl, with Grignard reagents of the general formula $R^1$—Mg—Hal, $R^1$ representing alkyl having 1 to 4 carbon atoms, and Hal in this instance representing chlorine or bromine. The reaction takes place smoothly on adding N,N,N',N'-tetramethylethylenediamine.

In the preparation of compounds I, in which $R^2$ and $R^3$ together form a carbonyl group and $R^1$ represents OH, $OR^7$ or $NR^8R^9$, it is also possible to proceed in such a manner that first compounds I, where $R^2$ and $R^3$ are carbonyl and $R^1$ is hydrogen, are oxidized by process variant (d), it being possible in principle to use the same oxidizing agents as are detailed for process variant (c), in particular those which can be used in combination with an aqueous solvent. In this context, it has proved to be particularly advantageous to use permanganates, for example $KMnO_4$, in an aqueous alkaline solution, such as, for example, in sodium hydroxide solution. The reaction usually takes place even at room temperature, but higher temperatures are necessary to obtain good yields. The reaction is advantageously carried out between 40° and 80° C. Toward the end of the reaction, excess oxidizing agent is usually destroyed by a mild reducing agent, such as, for example, $Na_2SO_3$. The reaction products are obtained in a pure crystalline form by acidifying the reaction solutions with mineral acid, such as, for example, 2 N HCl. The resulting carboxylic acids of the general formula I, with $R^1$ having the meaning of OH, can then optionally be converted into their esters by standard methods, for example by acid-catalyzed reaction with alcohols $R^7OH$, for example by heating the acid I in $R^7OH$ as the solvent, $R^7$ having the abovementioned meaning, to reflux, with the addition of sulfuric acid. However, it is also possible to use other known methods of esterification, for example the method of mixed anhydrides or the acid halide method. This applies correspondingly when the intention is to prepare from compounds I, with $R^1$ having the meaning OH, the corresponding carboxamides I, with $R^1$ having the meaning $NR^8R^9$, again, it is possible to use all the standard methods for the preparation of carboxamides from carboxylic acids.

Compounds I, in which $R^1$ has the meaning of hydrogen or alkyl having 1 to 4 carbon atoms and in which $R^2$ and $R^3$ together represent a carbonyl group, can be converted by process variant (e), using standard methods into those compounds I in which $R^2$ and $R^3$ represent $OR^{10}$, $SR^{10}$ or $NR^{10}R^{11}$, and $R^{10}$ and $R^{11}$ have the abovementioned meanings, or in which $R^2$ and $R^3$ together form a $-X-(CH_2)_m-X-$chain, with X and m having the abovementioned meanings, or in which $R^2$ and $R^3$ together form an imino group $=N-^{11}$. This involves using processes for producing acetals, thioacetals and aminals and for preparing Schiff's bases from carbonyl compounds. For forming acetals and thioacetals, it is advantageous to use the reaction, which is catalyzed by Lewis acids, of carbonyl compounds I with alcohols $HOR^{10}$ or thioalcohols $HSR^{10}$ in a solvent which is inert toward the reactants, such as, for example, chlorinated hydrocarbons, for example methylene chloride, in the presence of dehydrating agents such as, for example, $MgSO_4$, molecular sieves or $TiCl_4$. Mineral acids, such as $H_2SO_4$, are also suitable as catalysts, particularly for forming acetals.

In general, primary amines $H-NR^{10}R^{11}$ produce imines of the general formula I, with $R^2$ and $R^3$ having the meaning of $=N-R^{11}$, without the addition of catalysts or dehydrating agents, while secondary amines $H-NR^{10}R^{11}$, in particular diamines of the general formula $H-NR^{11}-(CH_2)_m-NR^{11}-H$, very readily form aminals. It is usually sufficient simply to mix the starting components in an inert solvent, such as, for example, methanol or $CH_2Cl_2$. The desired compounds can then be isolated by simply removing the solvent, advantageously by evaporation.

It is also possible, in all process variants, to use starting materials of the general formula II, III, IV, V or VI in which $R^4$ has the meaning

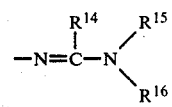

and $R^{14}$ to $R^{16}$ have the abovementioned meanings, for the preparation of compounds I, with $R^4$ having the meaning of $NH_2$.

The group

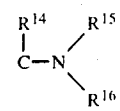

then has the meaning of a protective group for the $NH_2$ group. When this is used, it is necessary to follow the particular process variant by eliminating this protective group by hydrolysis. This is carried out in a manner known per se, advantageously by dissolving the compound which is to be hydrolyzed in aqueous alkali metal hydroxide solution, for example 2N sodium hydroxide solution, and then obtaining the compounds I, from which the protective group has been removed, in a crystalline form by acidifying the solution, for example with 2N hydrochloric acid.

If process variant (f) is carried out such that first phenols of the general formula XVII are converted into the sulfonyl chlorides XVIII, this can be achieved by, for example, initially allowing a sulfonating agent, such as, for example, sulfuric acid or chlorosulfonic acid, to act on the phenols XVII and subsequently adding a chlorinating agent, such as, for example, sulfuryl chloride, phosphorus oxychloride or chlorosulfonic acid. A process in which two or more equivalents of chlorosulfonic acid is allowed to act on the phenols XVII is preferably used. The solvents customary for chlorosulfonation, such as, for example, chlorinated hydrocarbons (for example methylene chloride), are used or the process is carried out without solvent, and this is particularly suitable with, for example, phenols XVII in which $R^2$ and $R^3$ together denote a carbonyl group. The reaction products XVIII are isolated by addition of a non-solvent, such as, for example, water, and then either reacted with amines

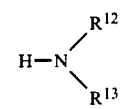

by standard methods, or converted, in analogy to the description under process variant a) for the conversion of compounds XIII via XIV into XI, into the sulfinic acids XIX which are converted into compounds I by alkylation with $R^4-X'$, $R^4$ and $X'$ having the abovementioned meanings.

In the present description, unless expressly mentioned otherwise, the term alkyl denotes alkyl groups having 1 to 8, preferably 1 to 4, in particular 1 or 2, carbon atoms, and the term halogen denotes fluorine, chlorine, bromine and iodine, preferably chlorine, bromine and iodine, in particular chlorine and bromine.

Apart from the compounds described in the exemplary embodiments, it is also possible according to the invention to obtain the compounds of the general formula I which are listed in the following table:

| $R^1$ | $R^2$ | $R^3$ | $R^4$ | $R^5$ | n |
|---|---|---|---|---|---|
| H | =O | | $NH_2$ | Cl | 2 |
| H | =O | | $NH_2$ | Br | 2 |
| H | =O | | $NH_2$ | F | 2 |

-continued

| R¹ | R² | R³ | R⁴ | R⁵ | n |
|---|---|---|---|---|---|
| H | =O | | NH₂ | I | 2 |
| H | =O | | CF₃ | tert. Bu | 2 |
| H | =O | | CF₃ | tert. Bu | 1 |
| H | =O | | CH₂—Cl | tert. Bu | 1 |
| H | OCH₃ | OCH₃ | CH₃ | tert. Bu | 2 |
| H | OCH₃ | OCH₃ | CH₃ | tert. Bu | 1 |
| H | SCH₃ | SCH₃ | CH₃ | tert. Bu | 2 |
| H | —O—(CH₂)₂—O— | | CH₃ | tert. Bu | 2 |
| H | —S—(CH₂)₂—S— | | CH₃ | tert. Bu | 2 |
| H | —O—(CH₂)₂—S— | | CH₃ | tert. Bu | 2 |
| H | =O | | NH₂ | C₃H₇ | 2 |
| H | =O | | NH₂ | iso-C₃H₇ | 2 |
| H | =O | | NH₂ | sec. C₄H₉ | 2 |
| H | =O | | NH₂ | tert.-Amyl | 2 |
| H | =O | | NH₂ | cyclo-C₅H₉ | 2 |
| H | =O | | NH₂ | cyclo-C₆H₁₁ | 2 |
| H | =O | | NH₂ | n-Bu | 2 |
| CH₃ | =O | | NH₂ | tert.-Bu | 2 |
| OH | =O | | NH₂ | tert.-Bu | 2 |
| OCH₃ | =O | | NH₂ | tert.-Bu | 2 |
| NH₂ | =O | | NH₂ | tert.-Bu | 2 |
| HN—CH₃ | =O | | NH₂ | tert.-Bu | 2 |
| N(CH₃)₂ | =O | | NH₂ | tert.-Bu | 2 |
| H | =O | | NHCH₃ | tert.-Bu | 2 |
| H | =O | | N(CH₃)₂ | tert.-Bu | 2 |
| H | —O—(CH₂)₂—O— | | NH₂ | tert.-Bu | 2 |
| H | —S—(CH₂)₂—O— | | NH₂ | tert.-Bu | 2 |
| H | —N—(CH₂)₂—N—<br>  |          |<br> CH₃     CH₃ | | NH₂ | tert.-Bu | 2 |
| H | —O—(CH₂)₃—O— | | NH₂ | tert.-Bu | 2 |
| H | —S—(CH₂)₃—S— | | NH₂ | tert.-Bu | 2 |
| H | OCH₃ | OCH₃ | NH₂ | tert.-Bu | 2 |
| H | SCH₃ | SCH₃ | NH₂ | tert.-Bu | 2 |
| H | =N—CH₃ | | NH₂ | tert.-Bu | 2 |
| H | =N—C₂H₅ | | NH₂ | tert.-Bu | 2 |
| H | =N—CH₃ | | CH₃ | tert.-Bu | 2 |
| H | =N—CH₃ | | CH₃ | tert.-Bu | 1 |

The compounds of the general formula I are of particular pharmacological and medical interest because they have cytoprotective activity. This signifies that they prevent damage to human or animal cells caused by exogenous or endogenous adverse effects or by age-related degenerative processes. For example, this type of action of the substances I to increase the resistance of surface epithelial cells can be used to prevent and heal damage to the mucosa of the gastrointestinal tract, such as, for example, from peptic ulcer and gastritis. However, the compounds can also have cytoprotective activity on other organs, for example in cases of acute or chronic damage to the liver, pancreas or vascular system.

Concerning the definition of the term "cytoprotection", reference is made to C. Johansson and S. Bergström in J. of Gastroenterol. 1982, Suppl. no. 77, pages 21 et seq.

Surprisingly, salicylaldehyde derivatives of simple structure, of the formula VII, are also suitable for the same purpose, namely for cytoprotection.

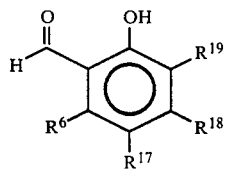

VII

The compounds of the formula I according to the invention and the compounds of the formula VII are cytoprotective agents which can be used as pharmaceuticals in human and veterinary medicine. They are administered enterally, for example orally with a tube or the like, or parenterally (injection into the vascular system, for example intravenously, or injections into muscle or transdermally) in doses of 0.01 to 30 mg/kg and day, preferably of 0.1 to 10 mg/kg and day, in particular 0.3 to 3 mg/kg and day, in capsules, coated tablets, tablets or solutions with various additives. They are suitable both for the treatment and for the prophylaxis of damage to the mucosa in the gastrointestinal tract, and of damage to the liver, pancreas and vascular system.

The compounds can be used alone or combined with other pharmaceutically active compounds, particular mention being made of those pharmaceuticals which, in addition to their therapeutic effect, display unavoidable harmful effects, for example non-steroidal antiinflammatory agents, such as aspirin or indometacin, or, for example, corticoids, such as cortisone, but cytostatic agents, such as, for example, 5-fluorouracil or cyclophosphamide, may also be mentioned.

EXAMPLE 1

2-formyl-4-(1,1-dimethylethyl)-6-methylsulfonylphenol 14.65 g (0.05 mol) of 2-aminomethyl-4-(1,1-dimethylethyl)-6-methylsulfonylphenol hydrochloride are dissolved in 100 ml of trifluoroacetic acid, 9 g (0.065 mol) of urotropine (hexamethylenetetraamine) are added, and the mixture is boiled under reflux for 2.5 h. Then 50 ml of 4 N hydrochloric acid are added, the mixture is again boiled under reflux for 10 minutes, and the reaction mixture is poured onto ice-water and filtered with suction. Pale yellow crystals of melting point: 134°–136° C.

Preparation of the starting compound
2-amino-4-(1,1-dimethylethyl)-6-methylsulfonylphenol hydrochloride (a) 3-(1,1-dimethylethyl)-6-methylbenzenesulfonyl chloride 12.3 g (0.075 mol) of 4-(1,1-dimethylethyl)phenol in 30 ml of methylene chloride are added dropwise, cooling in ice, to 16.5 ml of chlorosulfonic acid dissolved in 20 ml of methylene chloride. The mixture is stirred for 40 minutes and then poured onto ice-water. The organic phase is separated off, washed with water, dried with MgSO₄ and evaporated. The product is recrystallized from toluene petroleum ether.

Crystals of melting point: 75°–77° C.

(b) 3-(1,1-dimethylethyl)-6-methoxybenzenesulfinic acid 10.7 g (0.04 mol) of 3-(1,1-dimethylethyl)-6-methoxybenzenesulfonyl chloride are introduced into a solution of 15 g of Na₂SO₃ and 4 g of NaOH in 100 ml of water. After adding a little acetone, the mixture is heated on a steam bath for 30 minutes, then filtered and the pH is adjusted to 2–3 with concentrated hydrochloric acid.

Colorless crystals of melting point: 105°–107° C.

(c) 4-(1,1-dimethylethyl)-2-methylsulfonylanisole 17.4 g (0.076 mol) of 3-(1,1-dimethylethyl)-6-methoxybenzenesulfinic acid are suspended in 120 ml of acetone, and 13.3 ml (0.095 mol) of triethylamine and 8.5 ml (0.12 mol) of iodomethane are added. The mixture is stirred at room temperature for 2 hours and then poured onto ice-water. The precipitate which separates out is filtered off with suction and recrystallized from N-butanol.

White crystals of melting point: 111°–112° C.

(d) 4-(1,1-dimethylethyl)-2-methylsulfonylphenol 23.1 g (0.095 mol) of 4-(1,1-dimethylethyl)-2-methylsulfnylanisole are mixed with 60 g of pyridinium hydrochloride and heated at 210°–220° C. for 2 hours. The cooled mass is suspended in water, and the solid which separates out is filtered off with suction and extracted by boiling with petroleum ether. The solution is evaporated until crystallization starts.

White needles of melting point: 103°–104° C.

(e) 2-chloro-N-[5-(1,1-dimethylethyl)-2-hydroxy-3-methylsulfonylbenzyl]acetamide 13.5 g (0.06 mol) of 4-(1,1-dimethylethyl)-2-methylsulfonylphenol are dissolved in 100 ml of concentrated sulfuric acid. 6.63 g (0.054 mol) of 2-chloro-N-hydroxymethylacetamide are added and the mixture is stirred at room temperature for 10 minutes. It is then poured onto ice-water and the crude product is filtered off with suction and recrystallized from toluene.

Colorless crystals of melting point: 134°–135° C.

(f) 2-aminomethyl-4-(1,1-dimethylethyl)-6-methylsulfonylphenol hydrochloride 6.3 g (0.028 mol) of 2-chloro-N-[5-(1,1-dimethylethyl)-2-hydroxy-3-methylsulfonylbenzyl]acetamide in a mixture of 20 ml of concentrated hydrochloric acid and 40 ml of ethanol are boiled under reflux for 16 hours. The precipitated product is filtered off with suction and recrystallized from ethanol.

Colorless needles of melting point: 242°–243° C. (decomposition).

EXAMPLE 2

2-formyl-4-(1,1-dimethylethyl)-6-chloromethylsulfonylphenol 0.82 g (0.0025 mol) of 2-aminomethyl-4-(1,1-dimethylethyl)-6-chloromethylsulfonylphenol hydrochloride are reacted with urotropine in analogy to Example 1 to give 2-formyl-4-(1,1-dimethylethyl)-6-chloromethylsulfonylphenol.

Pale yellow crystals of melting point: 128°–129° C.

Preparation of the starting compound
2-aminomethyl-4-(1,1-dimethylethyl)-6-chloromethylsulfonylphenol hydrochloride (a) 2-chloromethylsulfonyl-4-(1,1-dimethylethyl)anisole 22.8 g (0.1 mol) of 3-(1,1-dimethylethyl)-2-methoxybenzenesulfinic acid, 23 g of Na$_2$CO$_3$ and 15 g (0.117 mol) of dichloroacetic acid are dissolved in 150 ml of H$_2$. The solution is slowly evaporated to dryness at a bath temperature of 160° C. The residue is again taken up in H$_2$O, and the solution is neutralized with a little dilute hydrochloric acid and extracted by shaking several times with ethyl acetate. After removing the solvent, the product is obtained as crystals.

Melting point: 114°–116° C.

(b) 2-chloromethylsulfonyl-4-(1,1-dimethylethyl)phenol 13.4 g (0.049 mol) of 2-chloromethylsulfonyl-4-(1,1-dimethylethyl)anisole are cleaved in analogy to Example 1(d) to give 2-chloromethylsulfonyl-4-(1,1-dimethylethyl)phenol.

Melting point: 94°–95° C.

(c) 2-chloro-N-[3-chloromethylsulfonyl-5-(1,1-dimethylethyl)-2-hydroxybenzyl]acetamide This compound is prepared in analogy to Example 1(e), and the crude product is recrystallized from toluene petroleum ether.

Melting point: 139°–140° C.

(d) 2-aminomethyl-4-(1,1-dimethylethyl)-6-chloromethylsulfonylphenol hydrochloride This compound is prepared in analogy to Example 1(f). Recrystallization from methanol/ether provides white crystals of melting point: 218°–219° C. (decomposition).

EXAMPLE 3

2-carboxy-4-(1,1-dimethylethyl)-6-methylsulfonylphenol 2.56 g (0.01 mol) of 2-formyl-4-(1,1-dimethylethyl)-6-methylsulfonylphenol are introduced into a solution of 1.58 g (0.01 mol) of potassium permanganate in 50 ml of 2N sodium hydroxide solution, and the mixture is heated on a steam bath for 30 minutes. The cooled solution is then adjusted to pH 2 with 2N hydrochloric acid and decolorized with concentrated Na$_2$SO$_3$ solution. The mixture is extracted three times with ethyl acetate, which is evaporated in vacuo and the residue is recrystallized from acetonitrile.

White crystals of melting point: 226°–227° C.

EXAMPLE 4

2-formyl-4-(1,1-dimethylpropyl)-6-methylsulfonylphenol 3.1 g (0.01 mol) of 2-aminomethyl-4-(1,1-dimethylpropyl)-6-methylsulfonylphenol hydrochloride are reacted with urotropine in analogy to Example 1.

Crystals of melting point 92°–94° C.

Preparation of the starting material
2-aminomethyl-4-(1,1-dimethylpropyl)-6-methylsulfonylphenol hydrochloride This compound is prepared in analogy to reaction sequence 1(a) to 1(f).

Melting point 187°–188° C. (decomposition).

EXAMPLE 5

2-formyl-4-bromo-6-methylsulfonylphenol 3.16 g (0.01 mol) of 2-aminomethyl-4-bromo-6-methylsulfonylphenol hydrochloride are converted into 2-formyl-4-bromo-6-methylsulfonylphenol in analogy to Example 1.

Melting point: 165°–166° C.

Preparation of the starting compound
2-aminomethyl-4-bromo-6-methylsulfonylphenol hydrochloride This subtstance is prepared in analogy to the reaction sequence described under Example 1(a) to 1(f).

Melting point: 228°–229° C.

EXAMPLE 6

2-formyl-4-(1,1-dimethylethyl)-6-ethylsulfonylphenol 0.615 g of 2-aminomethyl-4-(1,1-dimethylethyl)-6-ethylsulfonylphenol hydrochloride are reacted with 0.36 g of urotropine in 8 ml of trifluoroacetic acid to give 2-formyl-4-(1,1-dimethylethyl)-6-ethylsulfonylphenol in analogy to Example 1.

Melting point 92°–93° C.

The starting compound 2-aminomethyl-4-(1,1-dimethylethyl)-6-ethylsulfonylphenol hydrochloride is prepared in analogy to Example 1(a) to 1(f), but ethyl iodide is employed in place of methyl iodide in step 1(c) of the process.

Melting point: 203°–204° C. (decomposition).

EXAMPLE 7

2-formyl-4-isopropyl-6-methylsulfonylphenol 0.7 g (0.0025 mol) of 2-aminomethyl-4-isopropyl-6-methylsulfonylphenol hydrochloride are reacted with 0.45 g of urotropine in 8 ml of trifluoroacetic acid to give 2-formyl-4-isopropyl-6-methylsulfonylphenol in analogy to Example 1.

Melting point: 114°–116° C.

The starting material 2-aminomethyl-4-isopropyl-6-methylsulfonylphenol hydrochloride is prepared in analogy to Example 1a to 1f, but 4-isopropylanisole is employed in step 1(a) in place of 4-(1,1-dimethylethyl)anisole.

Melting point: 246°–247° C.

EXAMPLE 8

2-methoxycarbonyl-4-(1,1-dimethylethyl)-6-methylsulfonylphenol 1.0 g (0.003 mol) of 2-carboxy-4-(1,1-dimethylethyl)-6-methylsulfonylphenol prepared in Example 3 is dissolved in 6 ml of methanol, and heated under reflux with 0.1 ml of concentrated sulfuric acid for 2 days. The mixture is poured onto ice-water, and this is extracted with ethyl acetate, the solvent is removed in vacuo and the residue is subjected to chromatography on silica gel using ethyl acetate/toluene 4:1 as the eluting agent.

White crystals of melting point 107°–108° C.

EXAMPLE 9

2-formyl-4-(1,1-dimethylethyl)-6-methylsulfinylphenol 2.8 g (0.01 mol) of 2-aminomethyl-4-(1,1-dimethylethyl)-6-methylsulfinylphenol hydrochloride are reacted with 3 g of urotropine in trifluoroacetic acid in analogy to Example 1. However, the mixture is worked up as follows: the reaction mixture is poured onto ice-water, and the rubber-like mass which separates out is taken up in diethyl ether and the solution is washed with water until neutral. After evaporating off the solvent, the residue is subjected to chromatography on silica gel using the eluting agent toluene/ethyl acetate 4:1.

Pale yellow crystals of melting point: 100°–102° C.

It is also possible to use 4-(1,1-dimethylethyl)-2-methylsulfinylphenol in place of 2-aminomethyl-4-(1,1-dimethylethyl)-6-methylsulfinylphenol hydrochloride.

Preparation of the starting compound (a) 4-(1,1-dimethylethyl)-2-(methylsulfinyl)phenol 52 g (0.27 mol) of 4-(1,1-dimethylethyl)-2-hydroxythioanisole are dissolved in 300 ml of glacial acetic acid. While cooling in ice, 30 ml of 30% $H_2O_2$ are added dropwise. The mixture is stirred at room temperature for 2 hours, then poured onto ice-water and filtered with suction. Recrystallization from toluene.

White crystals of melting point: 149°–150° C.

(b) [5-(1,1-dimethylethyl)-2-hydroxy-3-methylsulfinylbenzyl]trimethylammonium iodide 11 g (0.052 mol) of 4-(1,1-dimethylethyl)-2-methylsulfinylphenol are boiled under reflux with 14 ml (0.1 mol) of a 40% strength aqueous solution of dimethylamine and 10 ml of a 35% strength aqueous solution of formaldehyde (0.1 mol) in 100 ml of ethanol for 1 hour. The solvent is removed in a rotary evaporator, the residue is taken up in 2N hydrochloric acid and the solution is extracted with ethyl acetate. The aqueous phase is again evaporated to dryness, and the residue is taken up in acetone, and 30 ml of iodomethane are added. The solution is left at room temperature for about 1 hour and then evaporated until crystallization starts.

White crystals of melting point: 183°–185° C.

(c) Methyl[3-azidomethyl-5-(1,1-dimethylethyl)-2-hydroxyphenyl]sulfoxide 8.9 g (0.022 mol) of the ammonium iodide obtained under b) are dissolved in 80 ml of dimethylformamide 5 g (0.08 mol) of sodium azide are added and the mixture is stirred at 100° C. for 30 minutes. It is then poured onto ice-water and filtered with suction. Without further purification, the yellowish product is dissolved while still slightly moist in 80 ml of methanol.

(d) 2-aminomethyl-4-(1,1-dimethylethyl)-6-methylsulfinylphenol hydrochloride

The methanolic solution of methyl[3-azidomethyl-5-(1,1-dimethylethyl)-2-hydroxyphenyl]sulfoxide obtained under (c) is mixed with a suspension of 1 g of 10% palladium on charcoal, and hydrogenation is carried out at room temperature and under atmospheric pressure for 2 hours. The mixture is filtered, the filtrate is evaporated and the residue is chromatographed on silica gel, the eluting agent used being a mixture of ethyl acetate and methanol (2:1). The free amine is initially produced (melting point: 192°–193° C.), which is converted into the title compound by recrystallization from 2N hydrochloric acid.

White crystals of melting point: 84°–86° C.

EXAMPLE 10

2-formyl-4-chloro-6-methylsulfonylphenol 2.4 g (0.009 mol) of 2-aminomethyl-4-chloro-6methylsulfonylphenol hydrochloride are reacted with 1.6 g of urotropine in 18 ml of trifluoroacetic acid to give 2-formyl-4-chloro-6-methylsulfonylphenol in analogy to Example 1.

Preparation of the starting compound 2-aminomethyl-4-chloro-6-methylsulfonylphenol hydrochloride is prepared in analogy to reaction sequence 1(a) to 1(f), but using 4-chloroanisole in stage 1(a) in place of 4-(1,1-dimethylethyl)anisole.

Melting point: 153°–154° C.

EXAMPLE 11

2-acetyl-4-(1,1-dimethylethyl)-6-methylsulfonylphenol 256 mg (1 mmol) of 2-formyl-4-(1,1-dimethylethyl)-6methylsulfonylphenol obtained in Example 1 are dissolved in 10 ml of absolute diethyl ether, and 328 mg (2 mmol) of N,N,N',N'-tetramethylethylenediamine are added, as is, under nitrogen, 1 ml of a 2.9 molar solution of methyl magnesium bromide in diethyl ether. The mixture is heated to reflux for 30 minutes, then poured onto ice-water, and the organic phase is separated off and washed to neutrality. After evaporating off the solvent, the residue is subjected to chromatography on silica gel using the eluting agent N-hexane/ethyl acetate 2:1. 2-(1-hydroxyethyl)2-4-(1,1-dimethylethyl)-6-methylsulfonylphenol of melting point 90° C. is obtained, and is immediately dissolved in 2ml of diethyl ether. 1 ml of a solution of 5 g of $Na_2Cr_2O_7.2H_2O$ and 3.75 ml of $H_2SO_4$ in 25 ml of $H_2O$ are added and the mixture is stirred at room temperature for 2 hours. It is then poured onto water, and the organic phase is separated off, washed to neutrality and the solvent is removed in vacuo. The residue is chromatographed on silica gel using the eluting agent ethyl acetate/toluene 4:1.

White crystals of melting point: 138°–140° C.

EXAMPLE 12

2-(2,5-dimethyl-1-imidazolidinyl)-4-(1,1-dimethylethyl)- 6-methylsulfonylphenol 1.28 g (0.005 mol) of 2-formyl-4-(1,1-dimethylethyl)-6-methylsulfonylphenol obtained in Example 1 are dissolved in 20 ml of methylene chloride, and 0.44 g (0.523 mol) of N,N'-dimethylethylenediamine is added. The mixture is stirred at room temperature for 1 h and the solvent is then evaporated off. The residue is crystallized from ether.

White crystals of melting point: 139°–140° C.

EXAMPLE 13

2-formyl-4-(1,1-dimethylethyl)-6-sulfamoylphenyl 2.84 g (0.01 mol) of 4-(1,1-dimethylethyl)-2-dimethylaminomethyleneaminosulfonylphenol are boiled under reflux with 1.4 g of urotropine in 10 ml of trifluoroacetic acid for 6 h. The mixture is poured onto ice-water, and the rubber-like mass which has separated out is taken up in ether, the solution is washed to neutrality and the solvent is removed in vacuo. The residue is chromatographed on silica gel using ethyl acetate/toluene 4:1 as the eluting agent. 2-formyl-4-(1,1-dimethylethyl)-6-dimethylaminomethyleneaminosulfonylphenol of melting point 182°–183° C. is obtained, and this is immediately dissolved in 2N sodium hydroxide solution. The solution is left on a steam bath for 30 minutes, and then the solution is acidified to pH 2–3 with 2N hydrochloric acid, and filtered with suction.

Pale yellow crystals of melting point: 147°–148° C.

Preparation of the starting compound 4-(1,1-dimethylethyl)2-dimethylaminomethyleneaminosulfonylphenol (a) 3-(1,1-dimethylethyl)-6-methoxybenzenesulfonyl chloride 12.3 g (0.075 mol) of 4-(1,1-dimethylethyl)anisole, dissolved in 30 ml of methylene chloride, are added dropwise, while cooling in ice, to 16.5 ml of chlorosulfonic acid dissolved in 20 ml of methylene chloride. The mixture is stirred for 40 minutes and then poured onto ice-water. The organic phase is separated off, washed with water, dried with $MgSO_4$ and evaporated. Recrystallization from toluene/petroleum ether provides crystals of melting point: 75°–77° C.

(b) 3-(1,1-dimethylethyl)-6-methoxybenzenesulfonamide 25.3 g (0.1 mol) of 3-(1,1-dimethylethyl)-6-methoxybenzenesulfonyl chloride are dissolved in a little acetone and slowly added dropwise to 100 ml of concentrated ammonia solution at room temperature. The mixture is stirred at room temperature for 30 minutes and then poured onto ice-water. After acidification with concentrated hydrochloric acid, the product is filtered off with suction. Isopropanol is used for recrystallization. White crystals of melting point 156°–158° C.

(c) 4-(1,1-dimethylethyl)-2-dimethylaminomethyleneaminosulfonylanisole 4.68 g (0.02 mol) of 3-(1,1-dimethylethyl)-6-methoxybenzenesulfonamide are dissolved in 50 ml of dimethylformamide, and 2.5 g (0.022 mol) of dimethylformamide dimethyl acetal are added. The mixture is left at room temperature for 30 minutes, then poured onto ice-water and filtered with suction.

White crystals of melting point: 134°–136° C.

(d) 4-(1,1-dimethylethyl)-2-dimethylaminomethyleneaminosulfonylphenol 2.98 g (0.01 mol) of 4-(1,1-dimethylethyl)-2-dimethylaminomethyleneaminosulfonylanisole are dissolved in 30 ml of methylene chloride, and 2.75 g (0.011 mol) of boron tribromide are added. The mixture is stirred at room temperature for 45 minutes and then excess boron tribromide is destroyed by cautiously adding methanol. The mixture of solvents is removed in vacuo and the residue is triturated with water. The product results in the form of pale yellowish crystals. Isopropanol is used for recrystallization.

Melting point: 162°–164° C.

EXAMPLE 14

2-formyl-4-methyl-6-methylsulfonylphenol 1.89 g of 2-aminomethyl-4-methyl-6-methylsulfonylphenol hydrochloride are reacted with 1.35 g of urotropine in 15 ml of trifluoroacetic acid in analogy to Example 1.

Pale yellow crystals of melting point: 150°–151° C.

The starting material, 2-aminomethyl-4-methyl-6-methylsulfonylphenol hydrochloride, is prepared in analogy to reaction sequence 1(a)-1(f).

Melting point: 227°–228° C.

EXAMPLE 15

2-Formyl-4-(1-methylpropyl)-6-methylsulfonylphenol 0.48 g (0.0016 mol) of 2-aminomethyl-4-(1-methylpropyl)-6-methylsulfonylphenol hydrochloride is reacted with 0.22 g of hexamethylenetetramine in 3 ml of trifluoroacetic acid in analogy to Example 1. Melting point: 68°–70° C.

The starting material 2-aminomethyl-4-(1-methylpropyl)-6-methylsulfonylphenol is prepared in analogy to reaction sequence 1 a–1 f. Melting point: 236°–238° C.

EXAMPLE 16

2-Formyl-4-(1,1-dimethylethyl)-6-isopropylphenol 0.4 g (0.0012 mol) of 2-aminomethyl-4-(1,1-dimethylethyl)-6-isopropylphenol hydrochloride is reacted with 0.17 g of hexamethylenetetramine in 2.5 ml of trifluoroacetic acid in analogy to Example 1. Melting point: 128°–130° C.

The starting material 2-aminomethyl-4-(1,1-dimethylethyl)-6-isopropylphenol hydrochloride is prepared in analogy to reaction sequence 1 a–1 f. Melting point: 209°–212° C.

EXAMPLE 17

2-Formyl-4-ethyl-6-methylsulfonylphenol 0.79 g (0.003 mol) of 2-aminomethyl-4-ethyl-6-methylsulfonylphenol hydrochloride is reacted with 0.42 g of hexamethylenetetramine in 6 ml of trifluoroacetic acid in analogy to Example 1. Melting point: 114°–116° C.

The starting material 2-aminomethyl-4-ethyl-6- methylsulfonylphenol hydrochloride is prepared in analogy to reaction sequence 1 a–1 f. Melting point: 101°–102° C.

EXAMPLE 18

4-Formyl-5-hydroxy-6-methylsulfonylindane 0.83 g (0.003 mol) of 4-aminomethyl-5-hydroxy-6-methylsulfonylindane hydrochloride is reacted with 0.42 g of urotropine in 6 ml of trifluoroacetic acid in analogy to Example 1. Melting point: 152°–153° C.

The starting material 4-aminomethyl-5-hydroxy-6-methylsulfonylindane hydrochloride is prepared in analogy to reaction sequence 1 a–1 f. Melting point: 244°–248° C.

EXAMPLE 19

N-Methyl-2-hydroxy-5-(1,1-dimethylethyl)-3-methylsulfonylbenzaldimine 2.56 g (0.01 mol) of 2-formyl-4-(1,1-dimethylethyl)-6-methylsulfonylphenol are dissolved in 30 ml of methanol. Gaseous methylamine is passed in, with stirring, until starting material is no longer detected by thin-layer chromatography. The methanol is removed in vacuo, and the oily residue is recrystallized from diethyl ether/petroleum ether. Yellow crystals of melting point 149°–151° C.

EXAMPLE 20

N-Ethyl-2-hydroxy-5-(1,1-dimethylethyl)-3-methylsulfonylbenzaldimine 2.56 g (0.01 mol) of 2-formyl-4-(1,1-dimethylethyl)-6-methylsulfonylphenol are reacted with ethylamine in analogy to Example 19. Yellow crystals of melting point 87°–88° C.

We claim:

1. A compound of the formula I

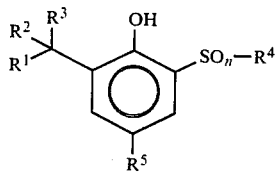

in which
R$^1$ represents hydrogen, alkyl having 1 to 4 carbon atoms, OR$^7$, where R$^7$ denotes hydrogen or alkyl having 1–4 carbon atoms, or NR$^8$R$^9$, where R$^8$ and R$^9$ are identical or different and denote hydrogen or alkyl having 1 to 4 carbon atoms;
R$^2$ and R$^3$ are identical or different and represent OR$^{10}$, NR$^{10}$R$^{11}$ or SR$^{10}$, where R$^{10}$ and R$^{11}$ are identical or different and represent alkyl having 1 to 8 carbon atoms, or
R$^2$ and R$^3$ together form a chain —X—(CH$_2$)$_m$—X—, where X represents O, S or NR$^{11}$, and m denotes 2 to 6, or together represent a carbonyl group =O or an imine group =N—R$^{11}$;
R$^4$ represents alkyl having 1 to 4 carbon atoms, cycloalkyl having 3 to 6 carbon atoms, alkenyl having 2 to 4 carbon atoms and up to 2 double bonds, and each having up to 3 halogen atoms, or represents NR$^{12}$R$^{13}$, where R$^{12}$ and R$^{13}$ are identical or different and denote hydrogen or alkyl having 1 to 4 carbon atoms;
R$^5$ represents alkyl having 1 to 10 carbon atoms or cycloalkyl having 3 to 8 carbon atoms and up to 8 ring members, or represents halogen; and
n is 1 or 2.

2. A compound as claimed in claim 1, wherein
R$^1$ represents hydrogen or OH;
R$^2$ and R$^3$ together form a carbonyl group or a chain

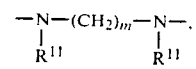

where m=2 or 3 and
R$^{11}$ denotes methyl or ethyl;
R$^4$ denotes methyl or NH$_2$;
R$^5$ denotes alkyl having 4 to 8 carbon atoms; and
n denotes 1 or 2.

3. A compound as claimed in claim 2, wherein R$^1$ represents hydrogen, R$^2$ and R$^3$ together represent the carbonyl group, R$^4$ represents methyl, R$^5$ represents alkyl having 4 to 8 carbon atoms and n represents 1 or 2.

4. A compound as claimed in claim 3, wherein R$^5$ denotes 1,1-dimethylethyl and n denotes 2.

5. A compound as claimed in claim 3, wherein R$^5$ is 1,1-dimethylethyl and n is 1.

6. A compound as claimed in claim 1, wherein R$^1$ represents hydrogen, R$^2$ and R$^3$ together represent the carbonyl group, R$^4$ represents chloromethyl, R$^5$ represents 1,1-dimethylethyl and n represents 2.

7. A compound as claimed in claim 2, wherein R$^1$ represents hydrogen, R$^2$ and R$^3$ together represent the carbonyl group, R$^4$ represents NH$_2$, R$^5$ represents 1,1-dimethylethyl and n represents 2.

8. A compound as claimed in claim 1, wherein
R$^1$ represents hydrogen or OH;
R$^2$ and R$^3$ together represent the carbonyl group =O;
R$^4$ denotes NR$^{12}$R$^{13}$, where R$^{12}$ and R$^{13}$ are identical or different and denote hydrogen or alkyl having 1–4 carbon atoms; and wherein
R$^5$ represents alkyl having 3 to 8 atoms; and
n represents 2.

9. The use of a compound of the formula I as claimed in claim 1 for the treatment and prophylaxis of damage to the mucosa of the gastrointestinal tract and of damage to the liver, the pancreas and the vascular system.

10. The use of a compound of the formula VII

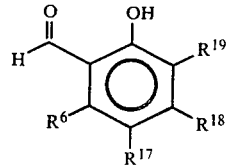

in which R$^6$, R$^{17}$, R$^{18}$ and R$^{19}$ represent hydrogen or halogen, as a cytoprotective agent.

11. The use of a compound as claimed in claim 10, where R$^6$ and R$^{18}$ are hydrogen, and R$^{17}$ and R$^{19}$ are hydrogen or halogen.

12. The use of salicylaldehyde as a compound as claimed in claim 10 as a cytoprotective agent.

13. The use of 2-formyl-4,6-dichlorophenol as a compound as claimed in claim 10 as a cytoprotective agent.

14. The use of 2-formyl-4,6-dibromophenol as a compound as claimed in claim 10 as a cytoprotective agent.

15. A compound of the formula I

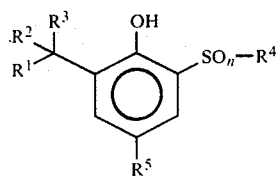

in which
- $R^1$ represents hydrogen, alkyl having 1 to 4 carbon atoms, $OR^7$, where $R^7$ denotes hydrogen or alkyl having 1–4 atoms, or $NR^8R^9$, where $R^8$ and $R^9$ are identical or different and denote hydrogen or alkyl having 1 to 4 carbon atoms;
- $R^2$ and $R^3$ are identical or different and represent $OR^{10}$, $NR^{10}R^{11}$ or $SR^{10}$ and $R^{11}$ are identical or different and represent alkyl having 1 to 8 carbon atoms, or $R^2$ and $R^3$ together represent a carbonyl group $=O$;
- $R^4$ represents alkyl having 1 to 4 carbon atoms, cycloalkyl having 3 to 6 carbon atoms, alkenyl having 2 to 4 carbon atoms and up to 2 double bonds, and each having up to 3 halogen atoms, or represents $NR^{12}R^{13}$, where $R^{12}$ and $R^{13}$ are identical or different and denote hydrogen or alkyl having 1 to 4 carbon atoms;
- $R^5$ represents alkyl having 1 to 10 carbon atoms or cycloalkyl having 3 to 8 carbon atoms and up to 8 ring members, or represents halogen; and
- n is 1 or 2, with the proviso that said compund is not 2-hydroxy-5-methyl-3-methylsulfinyl-acetophenone, 2-hydroxy-5-methyl-3-methylsulfonyl-acetophenone or 5-chloro-3-methylsulfonyl salicylic acid.

* * * * *